United States Patent [19]

Suovaniemi et al.

[11] 4,092,120
[45] May 30, 1978

[54] METHOD AND APPARATUS FOR ESTABLISHING FECAL OCCULT BLOOD

[75] Inventors: Osmo Suovaniemi, Helsinki; Pertti Virkola, Kauniainen; Herman Adlercreutz, Helsinki, all of Finland

[73] Assignee: Osmo Antero Suovaniemi, Helsinki, Finland

[21] Appl. No.: 743,470

[22] Filed: Nov. 19, 1976

[30] Foreign Application Priority Data

Dec. 8, 1975  Denmark .......................... 3440/75

[51] Int. Cl.² ...................... G01N 33/16; G01N 21/06
[52] U.S. Cl. .................................. 23/253 TP; 23/259; 23/230 B; 128/283
[58] Field of Search ............... 23/230 B, 253 TP, 259, 23/292; 195/139, 127; 220/8; 128/2 F, 2 W, 283

[56] References Cited

U.S. PATENT DOCUMENTS

| 3,097,070 | 7/1963 | Aldrich et al. ..................... 23/259 X |
| 4,007,012 | 2/1977 | Greenwald ............................ 23/259 |
| 4,038,149 | 7/1977 | Liner et al. ........................ 23/259 X |

FOREIGN PATENT DOCUMENTS 1,018,563  1/1966  United Kingdom ............... 128/2 W Primary Examiner—R.E. Serwin
Attorney, Agent, or Firm—Hopgood, Calimafde, Kalil, Blaustein and Lieberman

[57] ABSTRACT

A device is disclosed for the storage and testing of laboratory samples. The device includes a base plate having an aperture therethrough and having a recess extending into its bottom surface. A first raised wall member extends outwardly from the upper surface of the base plate to define a sample storage area over the aperture. A top cover is configured to fit over the upper surface of the base plate and includes a raised portion which extends into the raised wall portion on the base plate to compress the sample. A bottom cover fits snugly within the recess on the bottom surface. A sheet of testing material such as filter paper may be disposed within the recess beneath the bottom cover where it is brought in contact with the sample through the aperture in the base plate.

9 Claims, 4 Drawing Figures

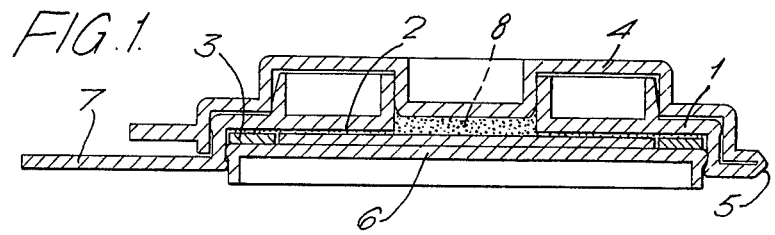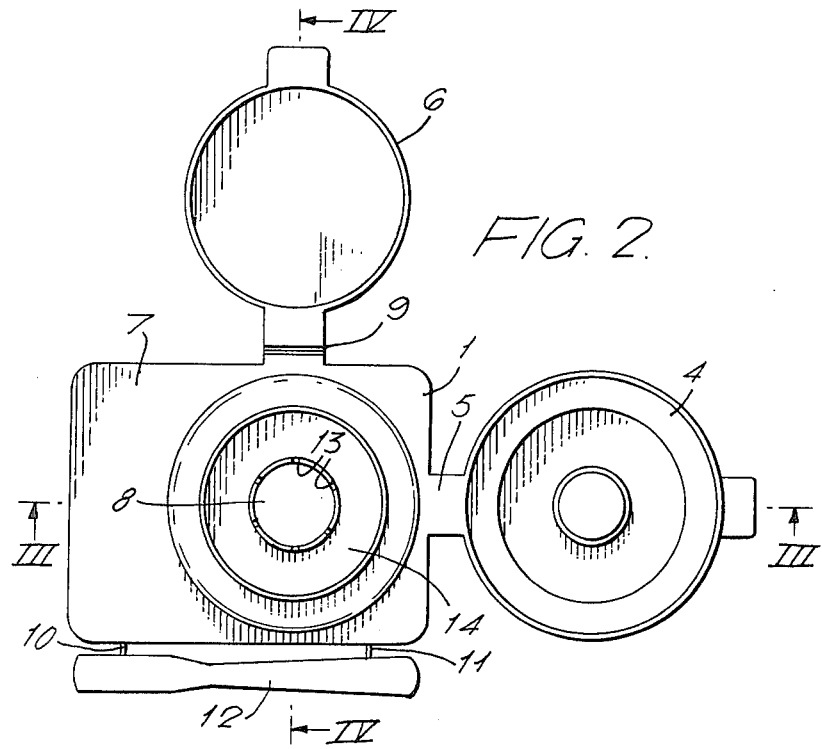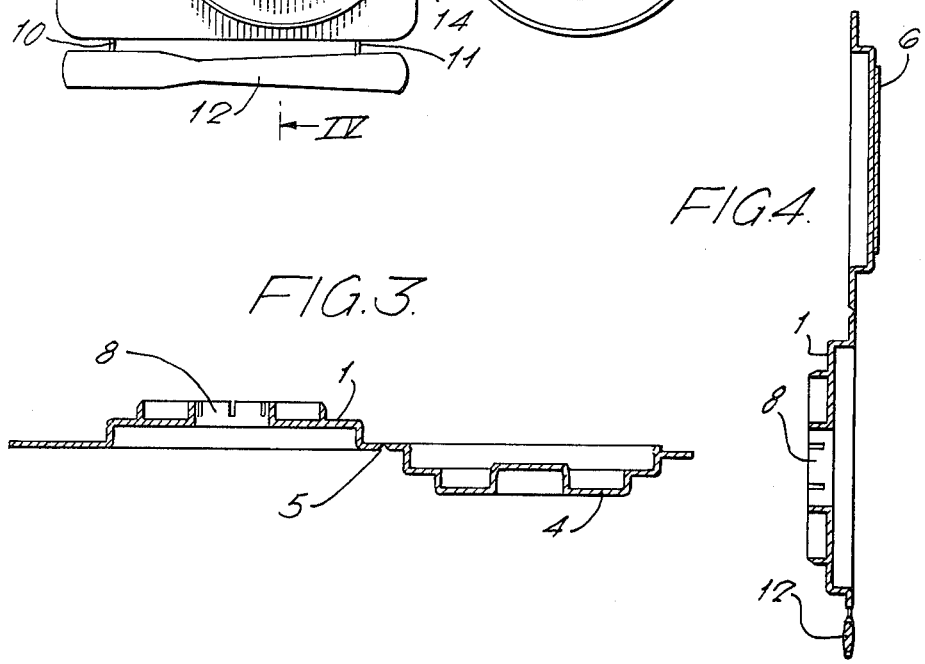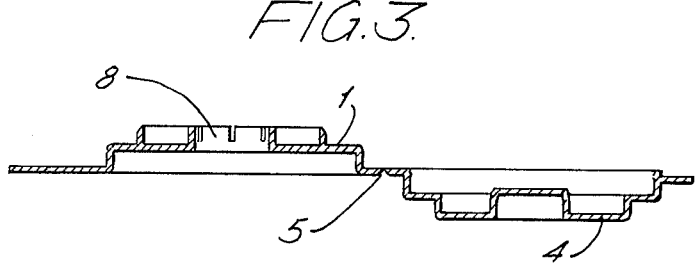

METHOD AND APPARATUS FOR ESTABLISHING FECAL OCCULT BLOOD

BACKGROUND OF THE INVENTION

The subject of the present invention is a method and an apparatus for storing samples for the purpose of later analysing such samples to estabish the presence of fecal occult blood.

The analysis of excrement, whether it be performed in open (non-hospital) conditions or under hospital conditions has been inconvenient, from the practical point of view, for the persons taking the samples. Such samples are also difficult to pack for possible transportation (mail transport or messenger service), and are inconvenient to handle in the laboratory during examination of the sample. Also tests to establish fecal occult blood have also been methodologically laborious, and the range of (blood quantity to excrement mass) has often been either too high or too low.

All the tests used to establish hemorrhages occuring within the area of the intestinal canal are based on the transformation of hemin into hematin in the presence of hydrogen peroxide. In this connection, certain organic compounds are oxidizable into coloured compounds. All the methods of establishing fecal occult blood currently in use involve a great number of difficulties both in respect of the taking, storage, and transportation of the fecal samples and in respect of the establishment of the existence of fecal occult blood. The range of use of such tests is limited. These prior art tests are described below.

In the Weber Test, a pea-sized clod of excrement is taken; the excrement is then emulsified by means of glacial acetic acid-ether, and the existence of the blood is established in a test tube by the guaiacol-hydrogen-peroxide test. A positive sample yields a blue or violet colour. In this test, excrement balls have to be transported. This method is too insensitive and, for this reason it is about to be phased out of use.

The Wagner test, which uses benzidine has been phased out of use because of its excessive sensitivity. Benzidine is, moreover, a carcinogenic substance.

In the Orthotoluidine test, a clod of excrement is homogenized in a test tube. The excrement suspension is then boiled for 5 minutes, and then cooled down to the room temperature. A colour reaction is then performed on a china plate. Orthotoluidine is also a carcinogenic substance.

In the Hematest[R] (Ames) tablet test excrement is spread onto a filter paper and, the Hematest reagent is placed onto the applied excrement layer. A few drops of water are then dropped onto the tablet. In a positive test a blue intermediate ring is produced around the reagent.

In the Hemoccult[R] (Smith-Kline & French Laboratories) filter paper test excrement is spread onto a paper treated with guaiac resin. The resulting cardboard package is then sealed and sent to the laboratory, where one side of the carboard box is opened and hydrogen peroxide is dropped onto the rear side of the filter paper. A blue colour ring results for a positive sample. The quantity of excrement to be placed into the carboard box cannot be regulated in this arrangement, and excrement may be extruded through the open sides of the box.

In the apparatus and method in accordance with the present invention, the above difficulties are circumvented and it is possible to perform tests, such as, bacteria cultures on the fecal sample prepared in accordance with this method and apparatus. The characteristics of the invention are described more fully below.

SUMMARY OF THE INVENTION

A device for the storage and testing of a laboratory sample includes a base plate having a top and a bottom surface, a recess formed in the bottom surface and an aperture extending therethrough. A first raised wall member extends outwardly from the top surface of the base plate and is disposed about and adjacent to the aperture to define a storage area for the sample. A first cover includes a raised portion which will extend into the storage area defined by the raised wall member to compress the sample when the first cover is placed over the top surface of the base plate. A second cover for the bottom surface of the base plate is configured to fit snugly within the recess in the bottom surface. Preferably, a sheet of testing material is mounted within the recess in the bottom surface so that a portion of the filter paper is exposed to the sample through the aperture in the baseplate.

BRIEF DESCRIPTION OF THE DRAWINGS

The invention is set forth in the following description with reference to the attached drawing, wherein FIG. 1 shows a sample storage, transportation and analysing vessel or device in accordance with the invention as a sectioned side view when the vessel is in a closed position.

FIG. 2 shows the device in accordance with FIG. 1 as viewed from the top when is it opened and on a smaller scale than that of FIG. 1.

FIG. 3 shows a sectional view of FIG. 2 along plane III—III, and

FIG. 4 shows a sectional view of FIG. 2 along plane IV—IV.

DETAILED DESCRIPTION OF THE INVENTION

FIG. 1 shows a cross-sectional view of a device in accordance with the invention in a closed position, which device can be used to contain a sample of excrement. The device in accordance with FIG. 1 comprises a base plate 1, on which there is mounted a piece of reagent paper 2 which may be supported by a support ring 3 if necessary. Against the top of base plate 1, a sample cover 4 is pressed tightly. The cover 4 may be connected to the base plate 1 by means of an elastic hinge joint 5. An analysis cover 6 is also pressed tightly against the bottom of base plate 1. On an extension to the base plate 1, there is an identification portion 7, on which it is possible to write the patient's name, fasten a name label, or to code the plate by some other means for the purpose of identification. In FIG. 1 the excrement sample is placed in a recessed space 8 which is enclosed by the base plate 1, the raised wall 13A, the sample cover 4 when it is in the closed position of FIG. 1 and by the reagent paper 2. The reagent paper may be supported by the analysis cover 6 when the cover 6 is in its closed position against the base plate 1. When the excrement sample is placed into the space 8 of the device of FIG. 1, the sample cover 4 is in the opened position. In FIG. 2 the device is shown as viewed from the top with cover 4 and 6 in their opened positions. In FIG. 2 the device is illustrated with the analysis cover 6 fastened to the base plate 1 by means of an elastic joint 9. The sample cover 4 is similarly fastened to the base plate 1 by means of an elastic joint 5. Fastened to the base plate 1 by means of small bridges 10 and 11, there is a spoon 12 which is detachable from the base plate by cutting off the bridges. This spoon is used for the purpose of taking the sample and putting same into the space 8. Any excess quantity of excrement from the sample is forced outwardly from the space 8 through the slits 13 in raised cylindrical wall 13A into the reserve space 14 by pressure from raised portion 15 which mates with recess 8 when the sample cover 4 is closed.

FIG. 4 shows a cross-section view in which the analysis cover 6 is connected to the base plate 1 by means of an elastic joint 9.

In FIGS. 1 to 4 an exemplifying embodiment of the present invention is shown as a device which is die-cast out of plastics. The principle of operation of this device is as described below.

The device is supplied to the user, for example, in the form as is seen from FIG. 1, so that it contains a base plate 1, against which the reagent paper 2 is placed, supported by the support ring 3 if necessary, and the sample cover 4 and the analysis cover 6 which are in their closed positions. The paper which may, for example be filter paper, functions as the sheet of reagent paper 2. The paper 2 has been treated, for example, by means of a solution of guaiac resin before the device is assembled or closed.

The user opens the sample cover 4 by grasping tab 5 and places the excrement sample into the space 8 and closes the sample cover 4. The user may shift the excrement by means of the spoon 12 shown in FIG. 2, which can be torn loose by the user from the base plate 1.

If an excessive quantity of excrement has been placed into the space 8 shown in FIG. 1, the excess of the excrement is squeezed outwardly from the space 8 through the slits 13 in wall member 13A into the reserve space 14 by pressure from raised member 15 when the sample cover 4 is closed. In this way, it is possible to get the desired quantity of excrement into the space 8 by proper adjustment of the volume of the space 8.

A raised ring-like wall 17 surrounds area 14 to enclose excess excrement entering this area. A shoulder 19 of cover 4 fits tightly over wall 17. The snug fit of raised portion 15 of cover 4 within recess 8 and shoulder 19 of cover 4 over wall 17 provides a tight fit over all areas where excrement may be present. In addition, a second downwardly extending shoulder portion 21 of cover 4 locks around the outer portion of base plate 1.

In a tight device in accordance with FIG. 1, it is easy to move and store the excrement sample without the sample being oxidized and dried, causing odors in the environment, or excrement being spread to the environment where, for example, it could cause an infection of bacteria. — The patient's name is written onto the identification portion 7, or any identification system is applied or fastened to same. The identification may also be attached to the storage or transport bag or box of the device.

In the laboratory the analysis cover 6 of the device which has heretofore remained closed is opened and hydrogen peroxide solution is dropped onto the exposed reagent paper 2. If the excrement contains, for example, about 2 to 3 ml of blood per 24 hours, a blue colour of a certain degree is formed on the reagent paper 2.

Before the blood test is made, it is possible to open cover 4 and to take from the device a sample of excrement, for example, to test for bacteria culture or for establishing the presence of eggs of worms. This sample can be taken either from space 8 or from the reserve space 14. It is also possible to take samples from reserve space 14 after the blood has been tested for in the excrement.

After the desired analyses have been made, the covers 4 and 6 of the device can be closed and the device can be destroyed in a convenient way, or it may be used again after it has been sterilized and provided with a new reagent paper. It is, however, easy and inexpensive to construct the device so that it is more economical to use it as a disposable item.

Of course, it is also possible to use the device for taking, transporting, storing, and/or analysing samples other than those of excrement.

Below, advantages of the method and apparatus in accordance with the present invention will be described:

When the sample is taken, a certain defined quantity of excrement is obtained so that the test is semi-quantitative. Any excess excrement is extruded from the sample space through the slits 13 into the closed reserve space 14 and does not effect the blood test. As can be seen in the drawings, the excrement is in contact with the reagent paper 2 only in recess 8.

The transportation of the sample can be performed safely in the tightly sealed package. The bacteria in the excrement cannot be spread outside the package, and the package can be forwarded in an ordinary letter envelope. The device can be constructed of unbreakable materials, for example out of plastics.

The reagents to be used are not dangerous. As the reagent medium, it is possible to use, for example, filter paper or any other appropriate material.

The sample remains moist in the air tight package and cannot be, for example, oxidized by the air. The package can also be made of plastics which are non-transparent to UV-light so that no decomposition due to the effect of light takes place in either the sample or in the reagent paper in the package which has been treated with guaiac resin.

The package can, at the same time, be used for transportation required for other analyses of excrement.

For example, the establishing of fecal occult blood can be performed without excrement being removed from the package, and placed for example, into test tubes in the laboratory. In this way the disturbing odor of the excrement can be reduced or eliminated in the surrounding environment.

The means for taking the sample, such as spoon 12, may be attached to the package, and the patient himself can conveniently take the sample.

The establishing of fecal occult blood is easy with the aid of the package of the invention and this test can be performed by less trained laboratory personnel. The series of colour patterns produced on the paper 2 in the package facilitates the interpretation of the results.

The reading of the results is made easier by the contact face of the sample having an equal area within recess 5 and, a black background which may be provided by the color of the package reduces disturbing color reactions on the reagent paper.

The identification of the patient can be attached to the device or to the transport or storage box of the device.

What I claim is:

1. A device for the storage and testing of a laboratory sample including:

a base plate having a top and a bottom surface, a recess in said bottom surface, and an aperture extending through said base plate;

a first raised wall member extending outwardly from said top surface of said base plate, said wall member being disposed about and adjacent to said aperture to define a storage area for said sample;

a first cover including a raised portion which extends into the storage area defined by said raised wall member to compress said sample when said first cover is placed over said top surface of said base plate; and a second cover configured to fit snugly within said recess in said bottom surface to cover said aperture.

2. A device as claimed in claim 1 in which said first raised wall member includes at least one aperture extending therethrough and in which a second raised wall member extends outwardly from said top surface of said base plate, said second wall member surrounding said first wall member to define a reserve space on said top surface of said base plate into which excess material from said sample is forced when said raised portion of said first cover extends into said storage space defined by said first wall member.

3. A device as claimed in claim 1 in which said first and second covers are attached to said base plate by flexible strips which serve as hinges.

4. A device as claimed in claim 1 in which said first cover includes a first outwardly extending portion which is configured to fit snugly against said second wall member so that said first cover seals said reserve space.

5. A device as claimed in claim 1 in which said top surface of said base plate includes a raised portion having an outer circumferential edge and an upper substantially planar surface, said first and second wall members being formed on said substantially planar surface of said raised portion and in which said first cover includes a second outwardly extending portion which is configured to fit snugly about said outer circumferential edge of said raised portion.

6. A device as claimed in claim 1 including an elongated applicator member for use in applying said sample to said storage area which is removably connected to said base plate.

7. A device as claimed in claim 1 including a sheet of testing material disposed within said recess in the bottom surface of said base plate such that a portion of said sheet is exposed through said aperture in said base plate.

8. A device as claimed in claim 7 in which said testing material is filter paper which has been treated with guaiac resin.

9. A device as claimed in claim 7 including a support ring disposed within said recess to hold said sheet of testing material in a predetermined position.

* * * * *

UNITED STATES PATENT OFFICE
CERTIFICATE OF CORRECTION

Patent No. 4,092,120      Dated May 30, 1978

Inventor(s) OSMO SUOVANIEMI, PERTTI VIRKOLA and HERMAN ADLERCREUTZ

It is certified that error appears in the above-identified patent and that said Letters Patent are hereby corrected as shown below:

Under "Foreign Application Priority Data"

change "Denmark" to --Finland--

Signed and Sealed this

Eighteenth Day of March 1980

[SEAL]

Attest:

SIDNEY A. DIAMOND

Attesting Officer      Commissioner of Patents and Trademarks